April 30, 1963 E. E. WILLIAMS Plant Pat. 2,255
APRICOT TREE
Filed Oct. 27, 1960
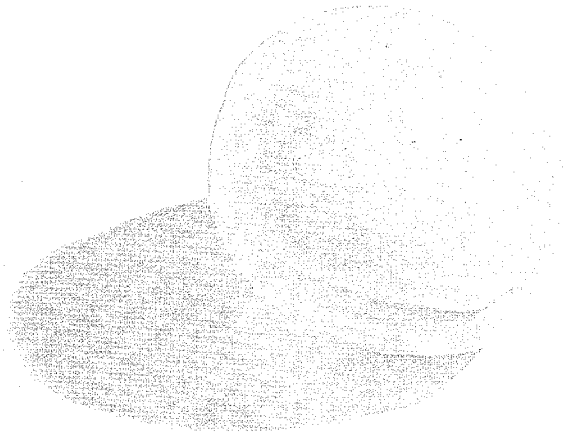

United States Patent Office

Plant Pat. 2,255
Patented Apr. 30, 1963

2,255
APRICOT TREE

Edgar E. Williams, Trinidad, Wash., assignor to Pacific Coast Nursery, Portland, Oreg., a firm doing business as a partnership Filed Oct. 27, 1960, Ser. No. 65,546
1 Claim. (Cl. 47—62)

The present invention relates to a new and distinct variety of apricot tree originated as a seedling of the variety known as Blenheim (unpatented). The new variety was discovered by me in 1942 in a cultivated orchard on my property in Trinidad, Washington.

The parent variety Blenheim is characterized by branches that spread slightly upright. The leaves have a distinct tip with a finely serrated edge and Blenheim has fruit productivity rated good to excellent.

The new variety is substantially identical in all respects with the aforementioned parent, except that the skin of the fruit of the new variety is characterized by a bright solid blush with a strong reddish orange undercolor and the fruit ripens about one week earlier than Moorpark (which is unpatented) and about 10 days to two weeks earlier than Blenheim in and adjacent Wenatchee, Washington.

Asexual reproduction of the new variety by grafting and budding in the Columbia River Basin in and adjacent Chelan County, Washington, establishes that the foregoing characteristics run true to form and are fixed and are transmitted through succeeding propagations.

The accompanying drawing shows a specimen of the fruit, in elevation.

The following is a detailed description of the new variety based upon observations of specimens grown in and adjacent Trinidad, Washington in the Columbia River Valley adjacent Chelan County, with color terminology in accordance with Nickerson Color Fan by Munsell Color Company as indicated, except where general color terms of ordinary dictionary significance are obvious:

Dates of first picking: June 30 as compared to July 3, of parent stock.

Tree: Fairly large, vigorous, upright, hardy, productive, regular bearing.

*Branches.*—Spread slightly upright.

*Leaves.*—Distinctive with a finely serrated edge and the color is moderate olive-green (7.5GY 4/4).

Flowers: Light pink and blossom date about the same as Moorpark.

Fruit: Moderately firm; 2 inches to 2⅜ inches in diameter; ovate with moderately tough skin; halves are slightly unequal with shallow suture; stem cavity is hollow to medium; pit and pit cavity are medium to large. Color—Forty percent of the surface is covered with a bright solid blush (7.5R 5/13); overall color is a strong reddish orange; undercolor 10YR 8/10.

Flesh: Moderately firm and juicy.

Use: Market and dessert.

Keeping quality: Medium.

I claim:

A new and distinct variety of apricot tree substantially as herein shown and described characterized as to novelty by its similarity to its parent variety (Blenheim) but distinguished therefrom by the substantially uniform attractive blush covering approximately 40% of the surface and a strong reddish orange undercoat, a harvesting date approximately 10 days to two weeks earlier than its parent variety.

No references cited.